United States Patent [19]

Hargrave et al.

[11] Patent Number: 5,747,488
[45] Date of Patent: May 5, 1998

[54] 2-ARYL-5,11-DIHYDRO-6H-DIPYRIDO[3,2-B:2',3'-E][1, 4]DIAZEPINES AND THEIR USE IN THE TREATMENT OF HIV INFECTION

[75] Inventors: Karl D. Hargrave, Brookfield; John R. Proudfoot, Newtown, both of Conn.

[73] Assignee: Boehringer Ingelheim Pharmaceuticals, Inc., Ridgefield, Conn.

[21] Appl. No.: 769,081

[22] Filed: Dec. 18, 1996

Related U.S. Application Data

[60] Provisional application No. 60/010,827, Jan. 30, 1996.

[51] Int. Cl.⁶ .................. C07D 243/06; C07D 401/14; A61K 31/415; A61K 31/55
[52] U.S. Cl. ............................................. 514/219; 540/555
[58] Field of Search ............................. 540/555; 514/219

[56] References Cited

U.S. PATENT DOCUMENTS 5,366,972  11/1994  Hargrave ............................. 514/220

OTHER PUBLICATIONS

K. Hargrave et al., "Novel Non–Nucleoside Inhibitors of HIV–1 Reverse Transcriptase. 1. Tricyclic Pyridobenzo–and Dipyridodiazepinones", *J. Med. Chem.*, 34, pp. 2231–2241 (1991).

Terrett et al., "Imidazo[2',3':6,5]Dipyrido[3,2–b:2',3'–e]–1,4Diazepines: Non–Nucleoside HIV–1 Reverse Transcriptase Inhibitors With Greater Enzyme Affinity Than Nevirapine", *Bioorganic & Medicinal Chemistry Letters*, 2, pp. 1745–1750 (1992).

De Lucca et al., Synthesis and Anti–HIV activity of pyrrolo–[1,2–d]–(1,4)–Benzodiazepin–6–ones, Bioorganic & Medicinal Chemistry Letters, vol. 2, No. 12, pp. 1639–1644, 1992.

*Primary Examiner*—Mukund J. Shah
*Assistant Examiner*—Deepak R. Rao
*Attorney, Agent, or Firm*—Robert P. Raymond; Alan R. Stempel; Mary-Ellen Devlin

[57] ABSTRACT

Disclosed are novel 2-aryl-5,11-dihydro-6H-dipyrido[3,2-b:2',3'-e][1,4]diazepines. These are useful in the of HIV infection. Exemplary compounds are:

8-Ethyl-1-methyl-10-(4-pyrazolyl)imidazo[2',3':6,5] dipyrido[3,2-b:2',3'-e][1,4]diazepine;

8-c-Propyl-1-methyl-10-(4-pyrazolyl)imidazo[2',3':6,5] dipyrido[3,2-b:2',3'-e][1,4]diazepine;

8-Ethyl-12-methyl-10-(4-pyrazolyl)imidazo[2',3':6,5] dipyrido[3,2-b:2',3'-e][1,4]diazepine; and, 8-c-Propyl-12-methyl-10-(4-pyrazolyl)imidazo[2',3':6,5] dipyrido[3,2-b:2',3 '-e][1,4]diazepine.

3 Claims, No Drawings

2-ARYL-5,11-DIHYDRO-6H-DIPYRIDO[3,2-B:2',3'-E][1, 4]DIAZEPINES AND THEIR USE IN THE TREATMENT OF HIV INFECTION

RELATED APPLICATIONS

The benefit of provisional application Ser. No. 60/010, 827, filed Jan. 30, 1996, is hereby claimed.

FIELD OF THE INVENTION

The invention relates to novel 2-aryl-5,11-dihydro-6H-dipyrido[3,2-b:2',3'-e][1,4]diazepines and pharmaceutically acceptable salts thereof, methods for preparing these compounds, the use of these compounds either alone or in combination with other anti-virals, immunomodulators, antibiotics, anti-infectives, or vaccines in the treatment of HIV infection, and to pharmaceutical compositions containing these compounds.

BACKGROUND OF THE INVENTION

The human disease, Acquired Immune Deficiency Syndrome (AIDS), is caused by the Human Immunodeficiency Virus (HIV), particularly the strain known as HIV-1.

Like other viruses, HIV-1 cannot replicate without commandeering the biosynthetic apparatus of the host cell it infects. It causes this apparatus to produce the structural proteins which make up the viral progeny. These proteins are coded for by the genetic material contained within the infecting virus particle, or virion. Being a retrovirus, however, the genetic material of HIV is RNA, not DNA as in the host cell's genome. Accordingly, the viral RNA must first be converted into DNA, and then integrated into the host cell's genome, in order for the host cell to produce the required viral proteins. The conversion of the RNA to DNA is accomplished through the use of the enzyme reverse transcriptase (RT), which is included within the infecting virion along with the RNA.

Reverse transcriptase has three known enzymatic functions; it acts as an RNA-dependent DNA polymerase, as a ribonuclease, and as a DNA-dependent DNA polymerase. Acting first as an RNA-dependent DNA polymerase, RT makes a single-stranded DNA copy of the viral RNA. Acting as a ribonuclease, RT frees the DNA just produced from the original viral RNA and destroys the original RNA. Finally, acting as a DNA-dependent DNA polymerase, RT makes a second, complementary DNA strand, using the first DNA strand as a template. The two strands form double-stranded DNA, which is integrated into the host cell's genome by another enzyme called integrase.

Compounds which inhibit the enzymatic functions of HIV-1 reverse transcriptase will inhibit replication of HIV-1 in infected cells. Such compounds are useful in the treatment of HIV-1 in infection in human subjects as demonstrated by the known RT inhibitors 3'-azido-3'-deoxythymidine (AZT), 2',3'-dideoxyinosine (ddI), and 2',3'-dideoxycytidine (ddC), the only drugs thus far approved for use in the treatment of AIDS and AIDS-related Complex (ARC).

As with any anti-viral therapy, use of RT inhibitors in the treatment of AIDS eventually leads to virus which is less sensitive to the given drug. Resistance (reduced sensitivity) to these drugs is the result of mutations which occur in the reverse transcriptase segment of the pol gene. The compounds of the present invention are highly potent against not only the wild-type (non-mutated) virus RT enzyme, but are also effective against the reverse transcriptase of many mutant viruses which have been observed in patients who have been treated with RT inhibitors.

Specifically, the compounds of the present invention are effective in inhibiting the Y181C mutant [in which the tyrosine (Y) at codon 181 has been mutated to a cysteine (C) residue] which has been the most commonly observed mutant in clinical studies following therapy with many non-nucleoside reverse transcriptase inhibitors. The compounds are also effective against other observed mutant enzymes which contain a single point mutation such as K103N, V106A, G190A, Y188C, or P236L.

PRIOR ART

U.S. Pat. No. 5,366,972; Hargrave et al., "Novel Non-Nucleoside Inhibitors of HIV-1 Reverse Transcriptase. 1. Tricyclic Pyridobenzo- and Dipyridodiazepinones", *J Med. Chem.*, 34, 2231 (1991); Terrett et al., "Imidazo[2',3':6,5]dipyrido[3,2-b:2',3'-e][1,4]diazepines: Non-Nucleoside HIV-1 Reverse Transcriptase Inhibitors with Greater Enzyme Affinity than Nevirapine", *Bioorg. Med. Chem. Lett.*, 2, 1745 (1992) describe compounds which are related to those of the invention.

SUMMARY OF THE INVENTION

A first aspect of the invention comprises novel 2-aryl-dipyridodiazepines. These possess inhibitory activity against both wild-type and mutant HIV-1 RT. A second aspect of the invention comprises methods for making these novel compounds. A third aspect of the invention is a method for treating HIV-1 infection which comprises administering, to a human being infected by HIV-1, a therapeutically effective amount of one of the above-mentioned novel compounds, either alone or in combination with other anti-viral agents. A final aspect of the invention comprises pharmaceutical compositions suitable for the treatment of HIV-1 infection comprising the above-mentioned compounds.

DESCRIPTION OF THE INVENTION

In one of its composition of matter aspects, the invention comprises 2-aryl-5,11-dihydro-6H-dipyrido[3,2-b:2',3'-e][1, 4]diazepines of the formula 1

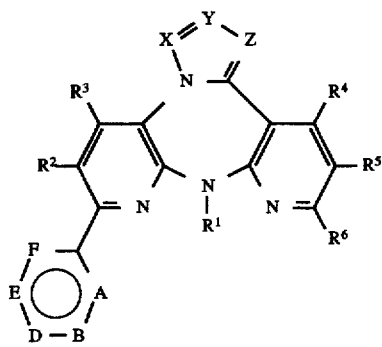

wherein,

A, B, D, E, and F form a six-membered aromatic ring wherein, A, B, D, E, and F are carbon, of which one or two of these carbon atoms are optionally unsubstituted or substituted with methyl, ethyl, amino, methyl- or ethylamino, dimethyl- or diethylamino, N-pyrrolidino, N-piperidino, N-morpholino, acetamido, acetamidomethyl, acetyl, acetyloxy, hydroxy, halogen, trifluoromethyl, hydroxymethyl, hydroxyethyl, methoxy, ethoxy, methyl- or ethylthio, methyl- or ethylsulfinyl, methyl- or ethylsulfonyl, methoxycarbonyl, ethoxycarbonyl, mono- or dimethylaminosulfonyl, aminosulfonyl, mono- or dimethylaminocarbonyl, aminocarbonyl, aminocarbonylethenyl, aminocarbonylpropenyl, aminocarbonylethyl, aminocarbonylpropyl or -cyclopropyl, arylaminocarbonyl (wherein aryl is phenyl optionally unsubstituted or substituted with methyl, halogen, hydroxy, methoxy, or amino, or is pyrrolyl, furanyl, thienyl, pyrrazolyl, imidazolyl, thiazolyl, oxazolyl, pyridyl, aminopyridyl, or chloropyridyl), cyano; or, A, B, D, E, and F form a six-membered heteroaromatic ring wherein, one of A, B, or D is nitrogen, and the four remaining positions are carbon, of which one of these carbon atoms is optionally unsubstituted or substituted with methyl, ethyl, amino, methyl- or ethylamino, dimethyl- or diethylamino, acetamido, acetamidomethyl, acetyl, acetyloxy, hydroxy, halogen, trifluoromethyl, hydroxymethyl, hydroxyethyl, methoxy, ethoxy, methyl- or ethylthio, methyl- or ethylsulfinyl, methyl- or ethylsulfonyl, methoxycarbonyl, ethoxycarbonyl, mono- or dimethylaminosulfonyl, aminosulfonyl, mono- or dimethylaminocarbonyl, aminocarbonyl, aminocarbonylethenyl, aminocarbonylethyl, arylaminocarbonyl or arylcarbonylamino (wherein aryl is phenyl optionally unsubstituted or substituted with methyl, halogen, hydroxy, methoxy, or amino, or is pyrrolyl, furanyl, thienyl, pyrrazolyl, imidazolyl, thiazolyl, oxazolyl, pyridyl, aminopyridyl, or chloropyridyl), or cyano, and of which a second of these carbon atoms is optionally unsubstituted or substituted with methyl, ethyl, or amino; or, A, B, D, E, and F form a six-membered heteroaromatic ring wherein, two of A, B, D, E, and F are nitrogen, and the three remaining positions are carbon, of which one of these carbon atoms is optionally unsubstituted or substituted with methyl, ethyl, amino, methyl- or ethylamino, dimethyl- or diethylamino, acetamido, acetamidomethyl, acetyl, acetyloxy, hydroxy, halogen, trifluoromethyl, hydroxymethyl, hydroxyethyl, methoxy, ethoxy, methyl- or ethylthio, methyl- or ethylsulfinyl, methyl- or ethylsulfonyl, methoxycarbonyl, ethoxycarbonyl, mono- or dimethylaminosulfonyl, aminosulfonyl, mono- or dimethylaminocarbonyl, aminocarbonyl, aminocarbonylethenyl, aminocarbonylethyl, arylaminocarbonyl or arylcarbonylamino (wherein aryl is phenyl optionally unsubstituted or substituted with methyl, halogen, hydroxy, methoxy, or amino, or is pyrrolyl, furanyl, thienyl, pyrrazolyl, imidazolyl, thiazolyl, oxazolyl, pyridyl, aminopyridyl, or chloropyridyl), or cyano, and of which a second of these carbon atoms is optionally unsubstituted or substituted with methyl, ethyl, or amino; or, A, B, D, E, and F form a five-membered heteroaromatic ring wherein F is a bond, and either A or B is nitrogen (unsubstituted or substituted with methyl, ethyl, or acetyl), oxygen, or sulfur, and the three remaining positions are carbon, wherein one or two of these carbon atoms are optionally unsubstituted or substituted with methyl, ethyl, hydroxymethyl, hydroxyethyl, trifluoromethyl, halogen, acetyl, methoxycarbonyl, ethoxycarbonyl, mono- or dimethylaminosulfonyl, aminosulfonyl, mono- or dimethylaminocarbonyl, aminocarbonyl, methyl- or ethylsulfinyl, methyl- or ethylsulfonyl, cyano, or nitro; or, A, B, D, E, and F form a five-membered heteroaromatic ring wherein F is a bond and one of A, B, D, and E is nitrogen, one is oxygen or sulfur, and the two remaining positions are carbon optionally unsubstituted or substituted with methyl, ethyl, hydroxymethyl, hydroxyethyl, trifluoromethyl, halogen, acetyl, methoxycarbonyl, ethoxycarbonyl, mono- or dimethylaminosulfonyl, aminosulfonyl, mono- or dimethylaminocarbonyl, aminocarbonyl, methyl- or ethylsulfinyl, methyl- or ethylsulfonyl, cyano, or nitro; or, A, B, D, E, and F form a five-membered heteroaromatic ring wherein F is a bond and two of A, B, D, and E are nitrogen (wherein one of the nitrogen atoms is unsubstituted or substituted with methyl, ethyl, acetyl, mono- or dimethylaminosulfonyl, methoxy- or ethoxycarbonyl, aminocarbonyl, alkylaminocarbonyl, or phenylaminocarbonyl), and the two remaining positions are carbon optionally unsubstituted or substituted with methyl, ethyl, hydroxymethyl, hydroxyethyl, trifluoromethyl, halogen, acetyl, methoxycarbonyl, ethoxycarbonyl, mono- or dimethylaminosulfonyl, aminosulfonyl, mono- or dimethylaminocarbonyl, amino-carbonyl, methyl- or ethylsulfinyl, methyl- or ethylsulfonyl, cyano, or nitro; or, A, B, D, E, and F form a five-membered heteroaromatic ring wherein F is a bond and two of A, B, D, and E are nitrogen, one of A, B, D, and E is oxygen or sulfur, and the remaining position is carbon optionally unsubstituted or substituted with methyl, ethyl, hydroxymethyl, hydroxyethyl, trifluoromethyl, halogen, acetyl, methoxycarbonyl, ethoxycarbonyl, mono- or dimethylaminosulfonyl, aminosulfonyl, mono- or dimethylaminocarbonyl, aminocarbonyl, methyl- or ethylsulfinyl, methyl- or ethylsulfonyl, cyano, or nitro; or, A, B, D, E, and F form a five-membered heteroaromatic ring wherein F is a bond and three of A, B, D, and E are nitrogen (wherein one of the nitrogen atoms is unsubstituted or substituted with methyl, ethyl, acetyl, mono- or dimethylaminosulfonyl, methoxy- or ethoxycarbonyl, aminocarbonyl, alkylaminocarbonyl, or phenylaminocarbonyl), and the remaining position is carbon optionally unsubstituted or substituted with methyl, ethyl, hydroxymethyl, hydroxyethyl, trifluoromethyl, halogen, acetyl, methoxycarbonyl, ethoxycarbonyl, mono- or dimethylaminosulfonyl, aminosulfonyl, mono- or dimethylaminocarbonyl, aminocarbonyl, methyl- or ethylsulfinyl, methyl- or ethylsulfonyl, cyano, or nitro; or, A, B, D, E, and F form a five-membered heteroaromatic ring wherein F is a bond and A, B, D, and E are nitrogen; or, A, B, D, E, and F form a five-membered heteroaromatic ring wherein F is a bond and A is nitrogen (wherein the nitrogen atoms is unsubstituted or substituted with methyl, ethyl, acetyl, mono- or dimethylaminosulfonyl, methoxy- or ethoxycarbonyl, aminocarbonyl, alkylaminocarbonyl, or phenylaminocarbonyl), oxygen, or sulfur, E is carbon or nitrogen, and B and D together form one side of a fused phenyl ring (which is either unsubstituted or substituted by alkyl or alkyloxy of 1 to 3 carbon atoms, amino, hydroxyl or halogen); and, X, Y, and Z form a ring, wherein, X is $CR^8$ or nitrogen, wherein $R^8$ is hydrogen, alkyl of 1 to 3 carbon atoms, c-propyl, or halogen; and, Y and Z are each independently $CR^9$ or nitrogen, wherein $R^9$ is hydrogen, methyl, or ethyl; and, $R^1$ is hydrogen, alkyl of 1 to 6 carbon atoms, fluoroalkyl of 1 to 6 carbon atoms and 1 to 3 fluorine atoms, cycloalkyl of 3 to 6 carbon atoms, oxetanyl, thietanyl, tetrahydrofuranyl, tetrahydrothienyl, tetrahydropyranyl, tetrahydrothiopyranyl, alkenylmethyl or alkynylmethyl of 3 to 6 carbon atoms, alkyloxyalkyl or alkylthioalkyl of 2 to 5 carbon atoms, alkanoyl or thioalkanoyl of 2 to 5 carbon atoms, cyano, cyanoalkyl of 2 to 5 carbon atoms, hydroxyalkyl or acyloxyalkyl wherein the alkyl moiety contains 2 to 6 carbon atoms and the acyl moiety contains 2 to 3 carbon atoms, oxazolyl, isoxazolyl, thiazolyl, aryl or arylmethyl (wherein the aryl moiety is phenyl, thienyl or furanyl, which is either unsubstituted or substituted by alkyl or alkyloxy of 1 to 3 carbon atoms, hydroxyl or halogen), or alkyloxycarbonylmethyl wherein the alkyl moiety contains 1 to 5 carbon atoms;

one of $R^2$ or $R^3$ is alkyl of 1 to 6 carbon atoms, cycloalkyl of 3 to 6 carbon atoms, alkenyl or alkynyl of 2 to 6 carbon atoms, trihalomethyl, hydroxyalkyl of 1 to 6 carbon atoms, alkyloxyalkyl or alkylthioalkyl of 2 to 6 carbon atoms, aryloxy(or thio)methyl (wherein the aryl moiety is phenyl, thienyl or furanyl, which is either unsubstituted or substituted by alkyl or alkyloxy of 1 to 3 carbon atoms, hydroxyl or halogen), arylmethyloxy (or thio)methyl or arylethyloxy(or thio)methyl (wherein the aryl moiety is phenyl, thienyl or furanyl, which is either unsubstituted or substituted by alkyl or alkyloxy of 1 to 3 carbon atoms, hydroxyl or halogen), alkyloxycarbonylalkyl wherein the alkyl moieties each contain 1 to 2 carbon atoms, carboxyalkyl or cyanoalkyl wherein the alkyl moieties each contain 1 to 5 carbon atoms, mono- or di-alkylaminocarbonylalkyl wherein the alkyl moieties each contain 1 to 2 carbon atoms, hydroxyl, mercapto, alkyloxy or alkylthio of 1 to 5 carbon atoms, hydroxyalkyloxy of 2 to 4 carbon atoms, alkanoyloxy of 2 to 4 carbon atoms, alkylsulfinyl or alkylsulfonyl of 1 to 4 carbon atoms, alkanoyl of 2 to 6 carbon atoms, alkyloxycarbonyl wherein the alkyl moiety contains 1 to 3 carbon atoms, mono- or di-alkylaminocarbonyl wherein each alkyl moiety contains 1 to 3 carbon atoms, aminoalkyl of 1 to 4 carbon atoms, mono- or di-alkylamino wherein each alkyl moiety contains 1 to 3 carbon atoms mono- or di-alkylaminoalkyl wherein each alkyl moiety contains 1 to 3 carbon atoms, imidazol-2-yl, imidazol-4-yl, aryl or arylalkyl (wherein the aryl moiety is phenyl, thienyl, furanyl, or pyridyl, which is either unsubstituted or substituted by alkyl or alkyloxy of 1 to 3 carbon atoms, hydroxyl, amino, or halogen, and the alkyl moiety contains 1 to 3 carbon atoms which may be unsubstituted or substituted with a methyl, hydroxyl, or amino groups), halogen, cyano, nitro, azido or carboxyl, with the other substituent being hydrogen, methyl or halogen; or, $R^2$ and $R^3$ are joined to form a cycloalkyl with a 3 or 4 carbon bridge; or, $R^2$ and $R^3$ are each hydrogen;

one of $R^4$, $R^5$ and $R^6$ is alkyl of 1 to 4 carbon atoms, alkenyl or alkynyl of 2 to 4 carbon atoms, trihalomethyl, hydroxyalkyl of 1 to 4 carbon atoms, alkyloxyalkyl or alkylthioalkyl of 2 to 4 carbon atoms, alkyloxycarbonylalkyl wherein the alkyl moieties each contain 1 to 2 carbon atoms, hydroxyl, amino, mono- or di-alkylamino wherein each alkyl moiety contains 1 to 2 carbon atoms, pyrrolidinyl, alkyloxy or alkylthio of 1 to 4 carbon atoms, hydroxyalkyloxy of 2 to 4 carbon atoms, alkanoyloxy of 2 to 4 carbon atoms, alkylsulfinyl or alkylsulfonyl of 1 to 4 carbon atoms, alkanoyl of 2 to 6 carbon atoms, alkoxycarbonyl wherein the alkyl moiety contains 1 to 3 carbon atoms, aminoalkyl of 1 to 4 carbon atoms, mono- or di-alkylaminoalkyl wherein each alkyl moiety contains 1 to 2 carbon atoms, halogen, cyano, nitro, azido or carboxyl, with the other two substituents being hydrogen; or, two of $R^4$, $R^5$ and $R^6$ are independently alkyl of 1 to 2 carbon atoms, trihalomethyl, alkyloxy or alkylthio of 1 to 2 carbon atoms, or halogen, with the remaining substituent being hydrogen; or, $R^4$, $R^5$ and $R^6$ are each hydrogen.

A subgeneric aspect of the invention comprises compounds of formula 1, wherein,

A, B, D, E, and F form a six-membered aromatic ring wherein, A, B, D, E, and F are carbon, of which one of these carbon atoms is optionally unsubstituted or substituted with methyl, ethyl, amino, methyl- or ethylamino, dimethyl- or diethylamino, acetamido, acetamidomethyl, acetyl, acetyloxy, hydroxy, halogen, trifluoromethyl, hydroxymethyl, methoxy, ethoxy, methyl- or ethylthio, methyl- or ethylsulfinyl, methyl- or ethylsulfonyl, methoxycarbonyl, ethoxycarbonyl, mono- or dimethylaminosulfonyl, aminosulfonyl, mono- or dimethylaminocarbonyl, aminocarbonyl, aminocarbonylethenyl, aminocarbonylethyl, arylaminocarbonyl (wherein aryl is phenyl optionally unsubstituted or substituted with methyl, halogen, hydroxy, methoxy, or amino, or is pyrrolyl, furanyl, thienyl, pyrrazolyl, pyridyl, aminopyridyl, or chloropyridyl), or cyano, and of which a second of these carbon atoms is optionally unsubstituted or substituted with methyl or ethyl; or, A, B, D, E, and F form a six-membered heteroaromatic ring wherein, one of A, B, or D is nitrogen, and the four remaining positions are carbon, of which one of these carbon atoms is optionally unsubstituted or substituted with methyl, ethyl, amino, methyl- or ethylamino, dimethyl- or diethylamino, acetamido, acetamidomethyl, acetyl, acetyloxy, hydroxy, halogen, trifluoromethyl, hydroxymethyl, methoxy, ethoxy, methyl- or ethylthio, methyl- or ethylsulfinyl, methyl- or ethylsulfonyl, methoxycarbonyl, ethoxycarbonyl, mono- or dimethylaminosulfonyl, aminosulfonyl, mono- or dimethylaminocarbonyl, aminocarbon aminocarbonylethenyl, aminocarbonylethyl, arylaminocarbonyl or arylcarbonylamino (wherein aryl is phenyl optionally unsubstituted or substituted with methyl, halogen, hydroxy, methoxy, or amino, or is pyrrolyl, furanyl, thienyl, pyrrazolyl, pyridyl, aminopyridyl, or chloropyridyl), or cyano, and of which a second of these carbon atoms is optionally unsubstituted or substituted with methyl, ethyl, or amino; or, A, B, D, E, and F form a six-membered heteroaromatic ring wherein, two of A, B, D, E, and F are nitrogen, and the three remaining positions are carbon, of which one of these carbon atoms is optionally unsubstituted or substituted with methyl, ethyl, amino, methyl- or ethylamino, dimethyl- or diethylamino, acetamido, acetamidomethyl, acetyl, acetyloxy, hydroxy, halogen, trifluoromethyl, hydroxymethyl, methoxy, ethoxy, methyl- or ethylthio, methyl- or ethylsulfinyl, methyl- or ethylsulfonyl, methoxycarbonyl, ethoxycarbonyl, mono- or dimethylaminosulfonyl, aminosulfonyl, mono- or dimethylaminocarbonyl, aminocarbonyl, aminocarbonylethenyl, aminocarbonylethyl, arylaminocarbonyl or arylcarbonylamino (wherein aryl is phenyl optionally unsubstituted or substituted with methyl, halogen, hydroxy, methoxy, or amino, or is pyrrolyl, furanyl, thienyl, pyrrazolyl, pyridyl, aminopyridyl, or chloropyridyl), or cyano, and of which a second of these carbon atoms is optionally unsubstituted or substituted with methyl, ethyl, or amino; or, A, B, D, E, and F form a five-membered heteroaromatic ring wherein F is a bond, and either A or B is nitrogen (unsubstituted or substituted with methyl or acetyl) or oxygen, and the three remaining positions are carbon, wherein one of these carbon atoms is optionally unsubstituted or substituted with methyl, ethyl, hydroxymethyl, hydroxyethyl, trifluoromethyl, halogen, acetyl, methoxycarbonyl, ethoxycarbonyl, mono- or dimethylaminosulfonyl, aminosulfonyl, mono- or dimethylaminocarbonyl, aminocarbonyl, methyl- or ethylsulfinyl, methyl- or ethylsulfonyl, cyano, or nitro; or, A, B, D, E, and F form a five-membered heteroaromatic ring wherein F is a bond and one of A, B, D, and E is nitrogen, one is oxygen or sulfur, and the two remaining positions are carbon, wherein one of these carbon atoms is optionally unsubstituted or substituted with methyl, ethyl, trifluoromethyl, halogen, acetyl, methoxycarbonyl, ethoxycarbonyl, mono- or dimethylamino-sulfonyl, aminosulfonyl, mono- or dimethylaminocarbonyl, aminocarbonyl, methyl- or ethylsulfinyl, methyl- or ethylsulfonyl, cyano, or nitro; or, A, B, D, E, and F form a five-membered heteroaromatic ring wherein F is a bond and two of A, B, D, and E are nitrogen (wherein one of the nitrogen atoms is unsubstituted or substituted with methyl, ethyl, or acetyl), and the two remaining positions are carbon, wherein one of these carbon atoms is optionally unsubstituted or substituted with methyl, ethyl, trifluoromethyl, halogen, acetyl, methoxycarbonyl, ethoxycarbonyl, mono- or dimethylaminosulfonyl, aminosulfonyl, mono- or dimethylamino-carbonyl, aminocarbonyl, methyl- or ethylsulfinyl, methyl- or ethylsulfonyl, cyano, or nitro; and, X, Y, and Z form a ring, wherein,
  X is $CR^8$, wherein $R^8$ is hydrogen, methy, ethyl, or halogen; and,
  Y and Z are each independently $CR^9$ or nitrogen, with the proviso that both Y and Z are not nitrogen, and wherein $R^9$ is hydrogen or methyl; and, $R^1$ is hydrogen, alkyl of 1 to 5 carbon atoms, fluoroalkyl of 1 to 5 carbon atoms, cycloalkyl of 3 to 5 carbon atoms, oxetanyl, thietanyl, alkenylmethyl or alkynylmethyl of 3 to 5 carbon atoms, alkyloxyalkyl or alkylthioalkyl of 2 to 4 carbon atoms, alkanoyl of 2 to 4 carbon atoms, hydroxyalkyl of 2 to 5 carbon atoms, aryl or arylmethyl (wherein the aryl moiety is phenyl, thienyl or furanyl, which is either unsubstituted or substituted by alkyl or alkyloxy of 1 to 3 carbon atoms, hydroxyl or halogen), or alkyloxycarbonylmethyl wherein the alkyl moiety contains 1 to 4 carbon atoms;

one of $R^2$ or $R^3$ is alkyl of 1 to 4 carbon atoms, alkenyl or alkynyl of 2 to 4 carbon atoms, trihalomethyl, hydroxyalkyl of 1 to 4 carbon atoms, alkyloxyalkyl or alkylthioalkyl of 2 to 4 carbon atoms, aryloxy(or thio) methyl (wherein the aryl moiety is phenyl, thienyl or furanyl, which is either unsubstituted or substituted by alkyl or alkyloxy of 1 to 3 carbon atoms, hydroxyl or halogen), arylmethyloxymethyl or arylethyloxymethyl (wherein the aryl moiety is phenyl, thienyl or furanyl, which is either unsubstituted or substituted by alkyl or alkyloxy of 1 to 3 carbon atoms, hydroxyl or halogen), alkyloxycarbonylalkyl wherein the alkyl moieties each contain 1 to 2 carbon atoms, hydroxyl, alkyloxy or alkylthio of 1 to 3 carbon atoms, hydroxyalkyloxy of 2 to 3 carbon atoms, alkanoyloxy of 2 to 3 carbon atoms, alkylsulfinyl or alkylsulfonyl of 1 to 3 carbon atoms, alkanoyl of 2 to 4 carbon atoms, alkyloxycarbonyl wherein the alkyl moiety contains 1 to 2 carbon atoms, aminoalkyl of 1 to 3 carbon atoms, mono- or di-alkylaminoalkyl wherein each alkyl moiety contains 1 to 2 carbon atoms, amino, mono- or di-alkylamino wherein each alkyl moiety contains 1 to 4 carbon atoms, or halogen, with the other substituent being hydrogen, methyl, or chloro; or, $R^2$ and $R^3$ are each hydrogen;
one of $R^4$, $R^5$ and $R^6$ is alkyl of 1 to 2 carbon atoms, vinyl, trifluoromethyl, hydroxyalkyl of 1 to 2 carbon atoms, hydroxyl, alkyloxy or alkylthio of 1 to 2 carbon atoms, hydroxyalkyloxy of 2 to 3 carbon atoms, alkanoyloxy of 2 to 3 carbon atoms, amino, mono- or di-alkylamino wherein each alkyl moiety contains 1 to 2 carbon atoms, or halogen, with the other two substituents being hydrogen; or, $R^4$, $R^5$ and $R^6$ are each hydrogen.

A particular subgeneric aspect of the invention comprises compounds of formula I wherein, A, B, D, E, and F form a six-membered aromatic ring wherein, A, B, D, E, and F are carbon, wherein the carbon atom at position B is optionally unsubstituted or substituted with methyl, ethyl, amino, methyl- or ethylamino, dimethyl- or diethylamino, acetamido, acetamidomethyl, acetyl, acetyloxy, hydroxy, halogen, trifluoromethyl, hydroxymethyl, methoxy, ethoxy, methyl- or ethylthio, methyl- or ethylsulfinyl, methyl- or ethylsulfonyl, methoxycarbonyl, ethoxycarbonyl, mono- or dimethylaminosulfonyl, aminosulfonyl, mono- or dimethylaminocarbonyl, aminocarbonyl, aminocarbonylethenyl, aminocarbonylethyl, arylaminocarbonyl (wherein aryl is phenyl optionally unsubstituted or substituted with methyl, halogen, hydroxy, methoxy, or amino, or is pyrrolyl, furanyl, thienyl, pyrrazolyl, pyridyl, aminopyridyl, or chloropyridyl), or cyano, and of which a second of these carbon atoms is optionally unsubstituted or substituted with methyl or ethyl; or, A, B, D, E, and F form a six-membered heteroaromatic ring wherein, one of A is nitrogen, and the four remaining positions are carbon, of which one of these carbon atoms is optionally unsubstituted or substituted with methyl or amino; and, A, B, D, E, and F form a five-membered heteroaromatic ring wherein F is a bond, and either A or B is nitrogen (unsubstituted or substituted with methyl or acetyl), and the three remaining positions are carbon, wherein one of these carbon atoms is optionally unsubstituted or substituted with methyl, trifluoromethyl, acetyl, methoxycarbonyl, ethoxycarbonyl, or cyano; or, A, B, D, E, and F form a five-membered heteroaromatic ring wherein two of A, B, D, and E are nitrogen (wherein one of the nitrogen atoms is unsubstituted or substituted with methyl or acetyl), and the two remaining positions are carbon, wherein one of these carbon atoms is optionally unsubstituted or substituted with methyl; and, X, Y, and Z form a ring, wherein,
  X is $CR^8$, wherein $R^8$ is hydrogen or methy; and,
  Y and Z are each independently CH or nitrogen, with the proviso that both Y and Z are not nitrogen; and,
$R^1$ is alkyl of 2 to 3 carbon atoms, or cycloalkyl of 3 to 4 carbon atoms;
$R^2$ is hydrogen, methyl, or chloro;
$R^3$ is hydrogen, methyl, trifluoromethyl, or chloro, with the proviso that $R^3$ is not trifluoromethyl or chloro when $R^2$ is chloro;
$R^4$ and $R^6$ are hydrogen; and
$R^5$ is hydrogen or amino.
Preferred compounds of formula I are:
  8-Ethyl-1-methyl-10-(4-pyrazolyl)imidazo[2',3':6,5]dipyrido[3,2-b:2',3'-e][1,4]diazepine;
  8-c-Propyl-1-methyl-10-(4-pyrazolyl) imidazo[2',3':6,5]dipyrido[3,2-b:2',3'-e][1,4]diazepine;
  8-Ethyl-12-methyl-10-(4-pyrazolyl) imidazo[2',3':6,5]dipyrido[3,2-b:2',3'-e][1,4]diazepine;
  8-c-Propyl-12-methyl-10-(4-pyrazolyl) imidazo[2',3':6,5]dipyrido[3,2-b:2',3'-e][1,4]diazepine.

Synthesis Of Compounds Of Formula I And Their Salts

The compounds of Formula I and their salts can be prepared by known methods or obvious modifications thereof. Methods A–C, described below, are illustrative of the methods for preparing the compounds. Other examples using the coupling reactions described below are known, for example, J. K. Stille, *Angew. Chem., Int. Ed. Engl.*, 25,508 (1986); A. M. Echavarren and J. K. Stille, *J. Am. Chem.Soc.*, 109, 5478 (1987); V. Farina and B. Krishnan, *J. Am. Chem. Soc.*, 113, 9585 (1991); and R. F. Heck, *Acc. Chem. Res.*, 12, 146 (1979). Another general method for aryl-aryl coupling, the Suzuki reaction, makes use of arylboronic acids in the presence of palladium-based catalysts and is exemplified, for example, in N. M. Ali, A. McKillop, M. B. Mitchell, R. A. Rebelo, and P. J. Wallbank, *Tetrahedron*, 48, 8117 (1992).

Method A

Compounds of formula 1, wherein A, B, D, E, F, X, Y, Z, and $R^1$ through $R^6$ are as defined above, may be obtained by condensing compounds of formula 2

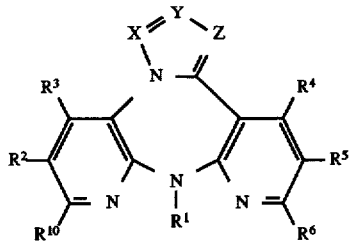

wherein X, Y, Z, and $R^1$ through $R^6$ are as defined above, and $R^{10}$ is chloro, bromo, iodo, or —OTf (wherein —OTf is —OSO$_2$CF$_3$) with tributyltin compounds of formula 3

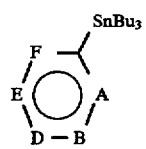

wherein A, B, D, E, and F are as defined above, in the presence of a palladium catalyst such as, tetrakis (triphenylphosphine)palladium(0), tetrakis(triphenylarsine)palladium(0), tetrakis(tri-2-furylphosphine)palladium(0), or bis(triphenylphosphine)palladium(II) chloride. These reactions are generally carried out under an inert atmosphere of argon or nitrogen, and in inert solvents such as 1,4-dioxane, tetrahydrofuran, N, N-dimethylformamide, N-methylpyrrolidinone, and the like, at temperatures generally between room temperature and the boiling point of the solvent. In some cases, the trimethyl tin compounds corresponding to the tributyltin compounds of formula 3 may be used.

Method B

In an alternative method, compounds of formula 1, wherein F is a bond, A, B, D, E, X, Y, Z, and $R^1$ through $R^6$ and $R^{10}$ are as defined above with the proviso that at least one of A and E is nitrogen, oxygen, or sulfur, may be obtained by condensing compounds of formula 2 which are as defined above, with compounds of formula 4

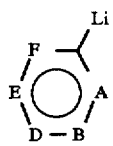

wherein A, B, D, E, and F are as defined above, in the presence of a palladium catalyst, such as tetrakis (triphenylphosphine)palladium(0), tetrakis(triphenylarsine)palladium(0), tetrakis(tri-2-furylphosphine)palladium(0), or bis(triphenylphosphine)palladium(II) chloride. These reactions are generally carried out in the presence of potassium or sodium acetate in inert solvents such as 1,4-dioxane, tetrahydrofuran, N, N-dimethylformamide, N-methylpyrrolidinone, and the like, and may be carried out in a sealed tube. The reaction temperatures are generally between 50° C. and 150° C.

Method C

In an alternative method, compounds of formula 1, wherein A, B, D, E, F, X, Y, Z, and $R^1$ through $R^6$ and $R^{10}$ are as defined above, may be obtained by condensing compounds of formula 2 which are as defined above, with zinc salt compounds of formula 5

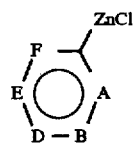

which are obtained by adding zinc chloride to the lithium salt of formula 4, wherein A, B, D, E, and F are as defined above. These reactions are generally carried in a manner analogous to Method A, i.e., under an inert atmosphere such as argon or nitrogen, and in the presence of a palladium catalyst, such as tetrakis(triphenylphosphine)palladium(0), tetrakis(triphenylarsine)palladium(0), tetrakis(tri-2-furylphosphine)palladium(0), or bis(triphenylphosphine)palladium(II) chloride. Inert solvents such as 1,4-dioxane, tetrahydrofuran, N, N-dimethylformamide, N-methylpyrrolidinone, and the like are generally used, and the reaction temperatures are generally between room temperature and the boiling point of the solvent.

Compounds of formula 6

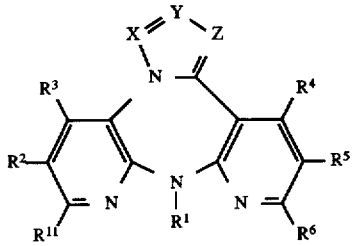

wherein X, Y, and Z form a ring, and, X is $CR^8$ or nitrogen, $R^8$ is hydrogen, alkyl of 1 to 3 carbon atoms, c-propyl, or halogen; and, Y and Z are each independently $CR^9$ or nitrogen, wherein $R^9$ is hydrogen, methyl, or ethyl, $R^{11}$ is chloro, bromo, iodo, or —$OCH_3$ and, wherein A, B, D, E, F, and $R^1$ through $R^6$ are as defined above, may be obtained by known methods, e.g., W. H. Jeffrey and J. Stanton, "Dibenzodiazepines and Other Tricyclic Diazepine Systems" in *Heterocyclic Compounds*, A. Rosowsky, Ed., John Wiley & Sond, New York, 1984, Vol 43, Part 2, pp. 1–717. A synthesis of pyrrol derivatives corresponding to compounds of formula 1 wherein X, Y, and Z are carbon, has been described for benzodiazepines in G. V. De Lucca and M. J. Otto, *Bioorg. & Med. Chem. Lett.*, 2, 1639 (1992).

It will be obvious to those skilled in the art that in some instances the reactions described in Methods A–C cannot be effected in the presence of reactive intermediates incompatible with the reaction conditions. In such cases, the reactive substituent must first be derivatized via known per se methods to contain a suitable protective group, which can then be subsequently removed.

Biological Properties

The above described compounds of formula 1 possess inhibitory activity against HIV-1 reverse transcriptase. When administered in suitable dosage forms, they are useful in the prevention or treatment of AIDS, ARC and related disorders associated with HIV-1 infection. Another aspect of the invention, therefore, is a method for preventing or treating HIV-1 infection which comprises administering to a human being, exposed to or infected by HIV-1, a prophylactically or therapeutically effective amount of a novel compound of Formula 1, as described above.

The compounds of formula 1 may be administered in single or divided doses by the oral, parenteral or topical routes. A suitable oral dosage for a compound of formula 1 would be in the range of about 0.5 mg to 1 g per day. A preferred oral dosage for a compound of formula 1 would be in the range of about 100 mg to 800 mg per day. In parenteral formulations, a suitable dosage unit may contain from 0.1 to 250 mg of said compounds, preferably 1 mg to 200 mg, whereas for topical administration, formulations containing 0.01 to 1% active ingredient are preferred. It should be understood, however, that the dosage administration from patient to patient will vary and the dosage for any particular patient will depend upon the clinician's judgement, who will use as criteria for fixing a proper dosage the size and condition of the patient as well as the patient's response to the drug.

When the compounds of the present invention are to be administered by the oral route, they may be administered as medicaments in the form of pharmaceutical preparations which contain them in association with a compatible pharmaceutical carrier material. Such carrier material can be an inert organic or inorganic carrier material suitable for oral administration. Examples of such carrier materials are water, gelatin, talc, starch, magnesium stearate, gum arabic, vegetable oils, polyalkylene-glycols, petroleum jelly and the like.

The pharmaceutical preparations can be prepared in a conventional manner and finished dosage forms can be solid dosage forms, for example, tablets, dragees, capsules, and the like, or liquid dosage forms, for example solutions, suspensions, emulsions and the like. The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound of formula 1 can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Microbial preservatives added may include benzalkonium chloride, thimerosal, chloro-butanol or phenylethyl alcohol.

Additionally, the compounds provided by the invention can be administered by suppository.

As stated before, the compounds provided by the invention inhibit the enzymatic activity of HIV-1 RT. Based upon testing of these compounds, as described below, it is known that they inhibit the RNA-dependent DNA polymerase activity of HIV-1 RT. It is known (data not shown) that they also inhibit the DNA-dependent DNA polymerase activity of HIV-1 RT.

Utilizing the Reverse Transcriptase (RT) Assay described below, compounds can be tested for their ability to inhibit the RNA-dependent DNA polymerase activity of HIV-1 RT. Certain specific compounds described in the Examples which appear below, were so tested. The results of this testing appear in Table I, below.

REVERSE TRANSCRIPTASE (RT) ASSAYS

Assay Theory:

Among the enzymes for which Human Immunodeficiency Virus (HIV-1) encodes is a reverse transcriptase (1), so-named because it transcribes a DNA copy from an RNA template. This activity can be quantitatively measured in a cell-free enzyme assay, which has been previously described (2), and is based upon the observation that reverse transcriptase is able to use a synthetic template [poly r(C) primed with oligo d(G)] to transcribe a radio-labelled, acid-precipitable DNA strand utilizing $^3$H-dGTP as a substrate. The assay described below utilizes the wild type (WT) enzyme, which is the predominant form of the enzyme observed in patients infected with HIV-1. Utilization of the mutant RT enzyme (Y181C, prepared by site-directed mutagenesis in which the tyrosine residue at codon 181 has been replaced by a cysteine residue) and analogous assay conditions allows compounds to be evaluated for their effectiveness at inhibiting this mutant enzyme.

Materials:

a) Preparation of the wild type enzyme Reverse transcriptase enzyme from the LAV strain of Human Immunodeficiency Virus (HIV-1)(1) was isolated from the bacterial strain JM109 (3) expressing the DNA clone pBRTprtl+(2) which is under the control of the lac promotor in the expression vector pIBI21 (4). An overnight culture grown in 2XYT medium (37° C., 225 rpm) (5) supplemented with 100 µg/mL ampicillin for positive selection is inoculated at a 1:40 dilution into M9 medium supplemented with 10 µg/mL thiamine, 0.5% casamino acids, and 50 µg/mL ampicillin (5). The culture is incubated (37° C., 225 rpm) until it reaches an OD540 of 0.3–0.4. At that time the repressor inhibitor IPTG (isopropyl β-D-thiogalactopyranoside) is added to 0.5 mM, and the mixture is incubated for 2 additional hours. Bacteria are pelleted, resuspended in a 5 mM Tris, 0.6 mM EDTA, 0.375M NaCl buffer and digested by the addition of lysozyme (1 mg/mL) for 30 minutes on ice. The cells are lysed by the addition of 0.2% NP-40 and brought to 1M NaCl.

After removal of the insoluble debris by centrifugation, the protein is precipitated by the addition of 3 volumes of saturated aqueous ammonium sulfate. The enzyme is pelleted, resuspended in RT buffer (50 mM Tris pH 7.5, 1 mM EDTA, 5 mM DTT, 0.1% NP-40, 0.1M NaCl, and 50% glycerol), and stored at −70° C. for further use.

b) Composition of 2X concentrated stock reaction mixture

| Stock Reagent | 2X Mix Concentration |
| --- | --- |
| 1M Tris pH 7.4 | 100 mM |
| 1M Dithiothrietol | 40 mM |
| 1M NaCl | 120 mM |
| 1% Nonidet P-40 | 0.1% |
| 1M MgCl | 4 mM |
| [poly r(C)/oligo d(G)](5:1) | 2 µg/mL |
| $^3$H-dGTP (81 µM) | 0.6 µM |

Assay Procedure:

The 2X concentrated stock reaction mixture is aliquoted and stored at −20° C. The mixture is stable and thawed for use in each assay. This enzyme assay has been adapted to a 96 well microtiter plate system, and has been previously described (6). Tris buffer (50 mM, pH 7.4), vehicle (solvent diluted to match the compound dilution), or compounds in vehicle are dispensed into 96-well microtiter plates (10 µL/well; 3 wells/compound). The HIV-1 RT enzyme is thawed, diluted in 50 mM Tris pH 7.4 so that fifteen µL of diluted enzyme contain 0.001 Unit (one unit is that amount of enzyme to transform 1 micromole of substrate per minute at 25° C.), and fifteen µL are dispensed per well. Twenty µL of 0.12–0.5M EDTA are added to the first three wells of the microtiter plate. EDTA chelates the Mg$^{++}$ present and prevents reverse transcription. This group serves as background polymerization which is subtracted from all other groups. Twenty-five ul of the 2X reaction mixture are added to all wells and the assay is allowed to incubate at room temperature for 60 minutes. The assay is terminated by precipitating the DNA in each well with 50 µL of 10% trichloracetic acid (TCA)(10% w/v) in sodium pyrophosphate (1% w/v). The microtiter plate is incubated for 15 minutes at 4° C. and the precipitate is fixed onto #30 glass fiber paper (Schleicher & Schuell) using a Skatron semi-automatic harvester. The filters are then washed with additional TCA (5%) containing sodium pyrophosphate (1%), rinsed with aqueous ethanol (70%), dried, and transferred to scintillation vials (6). Each vial receives 2 mL of scintillation cocktail and is counted in a Beckman beta counter.

The calculation for percent inhibition is as follows:

$$\% \text{ inhibition} = \frac{CPM \text{ Mean Test Value} - CPM \text{ Mean Control Value} \times 100}{CPM \text{ Mean Control Value}}$$

References:

1. Benn, S., et al., *Science* 230:949, 1985
2. Farmerie, W. G. et. al., *Science* 236:305, 1987
3. Yanisch-Perron, C., Viera, J., and Messing, J., *Gene* 33:103, 1985
4. International Biotechnologies, Inc., New Haven, Conn. 06535
5. Maniatis, T, Fritsch, E. F., and J. Sambrook, eds. *Molecular Cloning: A Laboratory Manual*, Cold Spring Harbor Laboratory, 1982
6. Spira, T., et. al. *J. Clinical Microbiology*, 25:97, 1987.

In order to confirm that compounds which are active in the RT Assay also have the ability to inhibit HIV replication in a living system, compounds according to the invention were also tested in the human T-Cell Culture (Syncytia) Assay described below. The results of this testing appear in Table I.

SYNCYTIA (HUMAN T-CELL CULTURE) ASSAY

Assay Theory:

Formation of syncytia is a feature of in vitro cultures of CD4+T-cells infected with HIV-1. In this assay, T-cells are treated with a putative replication inhibiting compound and then infected with HIV-1. After incubation, the culture is checked for the formation of syncytia. The absence or reduction in the number of syncytia is used as a measure of the test compound's ability to inhibit HIV replication.

Assay Method:

The target cells, designated c8166; are a subclone of human lymphoma cells of T-cell origin and are established at an initial density of $5 \times 10^4$ per 100 ul in RPMI 1640 (+10% fetal bovine serum) culture medium in 96 well flat bottom plates. A selected amount of test compound, dissolved in DMSO, is included. After 24 hours, 50–100 TCID$_{50}$'s (the dose that results in induced effect in 50% of test cultures) of the HTLV-IIIB strain of HIV-1 (2) are inoculated into each culture. Control cultures receive compound or virus only. Four days after virus challenge, cultures are visually examined for the frequency and distribution of virus-induced giant cell syncytia. The percent inhibition by the test compound is determined by comparison with control values. Confirmation of the presence or absence of virus replication is accomplished by harvesting the cell free culture fluids from all experimental groups to determine the presence or absence of infectious progeny through the induction of syncytia formation in secondary human T-cell cultures after 3 days.

References:

(1) M. Somasundaran and H. L. Robinson, *Science* 242, 1554 (1988).

(2) G. M. Shaw, R. H. Hahn, S. K. Arya, J. E. Groopman, R. C. Gallo and F. Wong-Staal, Science 226, 1165 (1984)

In order to assess the specificity of the enzyme inhibitory activity of the compounds provided by the invention, a few were tested, using known per se assay methods, for their ability to inhibit Feline Leukemia Virus-derived reverse transcriptase and Calf Thymus-derived DNA alpha-polymerase. None of the compounds so tested was observed to possess any inhibitory activity against these enzymes. These results indicate that the enzyme inhibitory activity of the compounds provided by the invention is directed rather specifically against HIV-1 RT.

In order to roughly assess the cytotoxicity of the compounds provided by the invention, several such compounds were tested in the MTT Assay described below. The results of this testing are reported in Table I, below. Compounds having a relatively high $CC_{50}$ are preferred.

MTT ASSAY

Assay Theory:

The MTT [3-(4,5-dimethylthiazol-2-yl)-2,5 diphenyl tetrazolium bromide] assay is based on cleavage of tetrazolium bromide by metabolically active cells, resulting in a highly quantitative blue color. This assay has been previously described (1) but has been optimized for the purposes of the testing reported herein.

Assay Method:

The H9 cell line (2), an established human lymphoma suspension cell line grown in RPMI 1640 supplemented with 10% fetal bovine serum, is used as the target cell line in the assay. Cells (100 µL) are plated in microtest plate wells at a concentration of $10^5$ cells per mL in the presence of varying concentrations of inhibitor. The cells are incubated at 37° C. in a humidified $CO_2$ incubator. Five days later, 20 µL of MTT (5 mg/mL in RPMI 1640, sonicated, 0.2 micron filtered, and stored at 4° C.) is added to each well. After 4 hours additional incubation at 37° C., 60 µL of Triton-X is added to each well and thoroughly mixed to aid the solubilization of the crystals. Absolute ethanol (5 µL) is added to each well and the resulting mixture is incubated for 30 minutes at 60° C. and immediately read on a plate reader (Dynatech) at a wavelength of 570 nm.

Data from this assay are used to generate a nonlinear regression analysis which yields an $CC_{50}$.

References:

1. Mosmann, Tim, J. Immunol. Methods, 65:55, 1983.
2. Jacobs, J. P., J. Natl. Cancer Inst., 34:231, 1965.

TABLE I

| Ex. No. | RT (WT) Assay | RT (Y181C) Assay | Syncytia Assay | MTT Assay |
|---|---|---|---|---|
| 1 | % inh. (1 µM) 95 | % inh. (1 µM) 88 | $IC_{50}$ (µM) NT | $CC_{50}$ (µM) >100 |

EXAMPLES

The following examples further illustrate the present invention and will enable others skilled in the art to understand it more completely. It should be understood, however, that the invention is not limited to the particular examples given below. Procedures for preparing starting materials not described below may be found in K. D. Hargrave, J. R. Proudfoot, J. Adams, K. G. Grozinger, G. Schmidt, W. Engel, G. Trummlitz, and W. Eberlein, U.S. application Ser. No. 740,828 (1991).

Example 1

8-Ethyl-1-methyl-10-(4-pyrazolyl)imidazo[2',3':6,5] dipyrido[3,2-b:2',3'-e][1,4]diazepine J-367 a) 10-Chloro-8-ethyl-1-methylimidazo[2',3':6,5]dipyrido [3,2-b:2',3'-e][1,4]diazepine A mixture of the 2-chloro-5,11-dihydro-11-ethyl-6H-dipyrido [3,2-b:2',3'-e][1,4]diazepine-6-thione (0.423 g) and propargylamine (0.2 mL) in butanol (10 mL) was heated at reflux for 8 h. The mixture was evaporated to dryness and fractionated directly over silica gel to give the product, which crystallized from ethyl acetate/isopropyl ether.

b) 8-Ethyl-1-methyl-10-(4-pyrazolyl) imidazo[2',3':6,5] dipyrido [3,2-b:2',3'-e][1,4]diazepine A mixture of 10-chloro-8-ethyl-1-methylimidazo[2',3':6,5]dipyrido[3,2-b:2',3'-e][1,4]diazepine (0.080 g), 4-(tributylstannyl) pyrazole (0.080 g), LiCl (0.059 g) and $Pd(PPh_3)_2Cl_2$ (0.007 g) in DMF (1 mL) was heated in a sealed tube at 120° C. for 16 h. The mixture was diluted with ethyl acetate, washed with water, dried (anhyd $Na_2SO_4$), filtered, and evaporated. The residue was fractionated over silica gel to give the title compound, which crystallized on trituration with ethyl acetate/isopropyl ether, mp 113°–115° C.

Example A

Capsules or Tablets

| A-1 Ingredients | Quantity | A-2 Ingredients | Quantity |
|---|---|---|---|
| Compound of Ex. 1 | 250 mg | Compound of Ex. 1 | 50 mg |
| Starch | 160 mg | Dicalcium Phosphate | 160 mg |
| Microcrys. Cellulose | 90 mg | Microcrys. Cellulose | 90 mg |
| Na Starch Glycolate | 10 mg | Stearic acid | 5 mg |
| Magnesium Stearate | 2 mg | Sodium Starch Glycolate | 10 mg |
| Fumed colloidal silica | 1 mg | Fumed colloidal silica | 1 mg |

The compound of Example 1 is blended into a powder mixture with the premixed excipient materials as identified above with the exception of the lubricant. The lubricant is then blended in and the resulting blend compressed into tablets or filled into hard gelatin capsules.

Example B

Parenteral Solutions

| Ingredients | Quantity |
|---|---|
| Compound of Example 1 | 500 mg |
| Tartaric acid | 1.5 g |
| Benzyl Alcohol | 0.1% by weight |
| Water for injection | q.s. to 100 mL |

The excipient materials are mixed with the water and thereafter the compound of Example 1 is added. Mixing is continued until the solution is clear. The pH of this solution is adjusted to 3.0 and is then filtered into the appropriate vials or ampoules and sterilized by autoclaving.

Example C

Nasal Solutions

| Ingredients | Quantity |
| --- | --- |
| Compound of Example 1 | 100 mg |
| Citric acid | 1.92 g |
| Benzalkonium chloride | 0.025% by weight |
| EDTA | 0.1% by weight |
| Polyvinylalcohol | 10% by weight |
| Water | q.s. to 100 mL |

The excipient materials are mixed with the water and thereafter the compound of Example 1 is added and mixing is continued until the solution is clear. The pH of this solution is adjusted to 4.0 and is then filtered into the appropriate vials or ampoules.

We claim:

1. 8-Ethyl-1-methyl-10-(4-pyrazolyl) imidazo[2',3':6,5] dipyrido[3,2-b:2',3'-e][1,4]diazepine, or a pharmaceutically acceptable addition salt thereof.

2. A method for treating HIV-1 infection which comprises administering, to a human being infected by HIV-1, a therapeutically effective amount of a compound as set forth in claim 1, or a pharmaceutically acceptable salt thereof.

3. A pharmaceutical composition suitable for treating HIV-1 infection which comprises a therapeutically effective amount of a compound as set forth in claim 1, or a pharmaceutically acceptable salt thereof, and a pharmaceutically acceptable carrier.

* * * * *